United States Patent [19]

Marhevka

[11] Patent Number: 5,017,369
[45] Date of Patent: May 21, 1991

[54] FILM-FORMING TEAT SEALER FOR PREVENTION OF MASTITIS AND USE THEREOF

[76] Inventor: Virginia C. Marhevka, 519 Crestview Dr., Maplewood, Minn. 55119

[21] Appl. No.: 372,283

[22] Filed: Jun. 27, 1989

Related U.S. Application Data

[63] Continuation of Ser. No. 21,169, Mar. 3, 1987, abandoned, which is a continuation-in-part of Ser. No. 801,938, Nov. 26, 1985, abandoned.

[51] Int. Cl.$^5$ ............................................... A61K 31/74
[52] U.S. Cl. ...................................................... 424/78
[58] Field of Search .......................................... 424/78

[56] References Cited

U.S. PATENT DOCUMENTS

| | | | |
|---|---|---|---|
| 3,911,107 | 10/1975 | Krezanoski | 424/78 |
| 4,022,199 | 5/1977 | Fetty | 128/132 R |
| 4,113,854 | 9/1978 | Andrews et al. | 424/78 |
| 4,311,709 | 1/1982 | Dybas et al. | 514/649 |
| 4,442,125 | 4/1984 | Thiele | 514/560 |

Primary Examiner—Stanley J. Friedman
Assistant Examiner—Kevin E. Weddington

[57] ABSTRACT

The disclosed teat sealer comprises:
a major amount (e.g. >65 wt.-%) aqueous solvent medium, and more than 1 wt.-% but less than about 16 wt.-% (preferably 2-12 wt.-%) partially hydrolyzed grade polyvinyl alcohol containing at least about 2 mole-% (e.g. 4-30 mole-%) residual vinyl acetate units dissolved in the aqueous medium.
an antimicrobially effective amount (e.g. 0.1-10%) of antimicrobial agent, such as a biguanidine salt which is compatible with aqueous polyvinyl alcohol;
from 0 to about 10% by weight of an opacifying agent such as a polymeric latex containing 15-70% by weight polymer solids, the latax being uniformly distributed through the aqueous medium in a stable manner, and
optionally (but preferably) a water-soluble dye dissolved in the aqueous medium to impart to the composition a color such as blue.

This teat sealing composition is effective against a variety of mastitis organisms and is strongly adherent to bovine teat skin under field conditions but is also easily removed with a simple water-washing technique. In using the composition, the teats of the animal are coated in a conventional manner, and the resulting coating is permitted to dry to an adherent film. A plug-like deposit forms at the teat end. This deposit adheres even more strongly to the animal's teats than the rest of the coating.

11 Claims, No Drawings

FILM-FORMING TEAT SEALER FOR PREVENTION OF MASTITIS AND USE THEREOF

CROSS REFERENCE TO RELATED APPLICATIONS

This application is a continuation of my copending application Ser. No. 07/021,619, filed Mar. 3, 1987, now abandoned, which is a continuation-in-part of my copending application Ser. No. 06/801,938, filed Nov. 26, 1985, now abandoned.

FIELD OF THE INVENTION

This invention relates to a prophylactic treatment for mastitis in mammals such as cows. An aspect of this invention relates to a coating for the teat of a cow that will protect the udder from mastitis-causing organisms between milkings. Another aspect of this invention relates to a coating composition especially suited to this prophylactic treatment, e.g. a water-based teat dip containing a film-forming polymer and an antimicrobial agent.

DESCRIPTION OF THE PRIOR ART

It is well known that teat dips (which include sprays and other coating compositions) can be an effective treatment for mastitis in mammals. The most important commercial application of this area of veterinary medicine lies in the treatment of cow udders. When a cow becomes infected and gets a case of mastitis, it has to be taken out of production, resulting in significant economic losses for the dairyman.

Persons skilled in the art of bovine mastitis treatment can conveniently divide teat dips into two broad classifications. First, there are those teat dips which are antimicrobial and are applied to kill microorganisms already present in the teat canal or on the surface of the teat skin—particularly microorganisms such as coliforms (which are almost unavoidably present in any dairy herd environment) and various species of Staphylococcus, Streptococcus, and Pseudomonas which can cause mastitis. The antimicrobial dip is typically applied after milking.

A second type of teat dip is a film-forming or coating composition which may or may not be antimicrobial—indeed, oftentimes this type of coating composition contains no biocidal agent whatever. The purpose of the film-forming composition is to provide prophylaxis by sealing the teat off from its environment. The film which forms on the surface of the teat serves as a shield or barrier through which mastitis - causing organisms cannot penetrate. Recent studies of treated and untreated dairy cows have established that certain of these barrier-type teat dips are reasonably effective against certain mastitis causing organisms, while other barrier-type formulations are completely ineffective and may be essentially worthless ( e.g. because of a tendency to form cracks in the film or to irritate the teat skin). The more effective teat dips appear to be made up either of organic polymeric latex solids (dispersed, suspended, or emulsified in water) or of water-compatible organic film-forming natural or synthetic materials. Typically these more effective teat dips form relatively flexible films which do not irritate teat skin or tissue and which can be stripped off the treated teats. By moistening the film and then peeling it off.

Among the materials used in barrier-type or film-forming type teat dips are solubilized lipids, vinyl pyrrolidone and other vinyl polymers, protein hydrolyzate, natural and synthetic gums, water—and alcohol—soluble polymers, unsaturated triglyceride oils, cellulose derivatives, and acrylic polymer latexes. A considerable degree of success has already been obtained with a barrier teat dip containing an acrylic-type polymer in aqueous latex form. The latex forms a flexible (almost rubbery) film on the teat skin, which film can be peeled off after moistening the area. However, removal of the teat-protecting film by peeling can be inconvenient and troublesome. Tiny pieces of the peeled film can find their way into the milk or into the milking machine, resulting in clogging of milking machinery or milk separators. Moreover, unless the film-forming teat dip has been dyed a color which contrasts sharply with the whitish color of cows' milk, the pieces or crumbs of film-forming latex or other polymeric solids can be mistaken for deposits of milk solids. Unfortunately, antimicrobial agents are not necessarily compatible with latexes and water-soluble or water-dispersible polymers13 that is, the presence of the antimicrobial agent (which is typically a salt-like or other highly polar compound) may cause destabilization of a latex or a dispersion or even a solution. As a result, some of the most effective and otherwise desirable film-formers must be formulated without bactericides and must rely entirely on barrier or shielding effects for mastitis prophylaxis. In some cases a .bactericide can be present, but it may have to be selected for a certain critical type of compatibility rather than for its spectrum of activity.

There is therefore still a need for a film-forming barrier-type teat dip composition which is compatible with a variety of antimicrobial agents, is effective against a wide spectrum of mastitis causing organisms, is removable by a simple water-washing technique not involving any peeling, and yet has sufficient adherence to the teat skin to withstand premature stripping or loss of integrity due to environmental conditions which can include rain, wet pastureland, rubbing, complete immersion in ponds, lakes, and streams, and the like. Filling this need involves striking effective balance between a film-former which is sufficiently water-sensitive to be stripped off with a conventional udder wash but not so water-sensitive as to be inadvertently washed or peeled off between milkings. It is known, for example, that cows like to swim in lakes, ponds, and streams. A too-soluble polymeric film could not possibly survive even a brief swim. A water-resistant film, on the other hand, may fail to dissolve under any conditions and may require removal by a purely physical step such as peeling.

The following references are considered to be representative of the state of this art. Typical disclosures of an iodophor-type or other disinfectant after-milking teat dips (aimed at destroying any pathogens remaining on the teats after milking) can be found in British patent 1,144,637 (Kilco Chemicals Ltd.), published on Mar. 5,1969, Neave et.al., *J. Dairy Science* 52:696 (1969), Dodd et.al., "Mastitis Control", Biennial Reviews - 1970, University of Reading, England, National Inst. of Res. in Dairying, pp. 21-57, U.S. Pat. No. 4,258,056 (Lentsch), issued Mar. 24, 1981, U.S. Pat. No. 4,376,787 (Lentsch), issued Mar. 15, 1983, U.S. Pat. No. 4,446,153 (Yang), issued May 1, 1984. These references describe a variety of antimicrobial agents, emollients, thickeners, coloring agents, etc. The thickeners include water-soluble or water-dispersible polymers, and some of the proposed emollients may have film-forming properties, but that is not their primary purpose. Typical disclosures of intermilking (dry period) and/or protective (barrier-type) film-forming teat dips or teat "sealers" can be found in U.S. Pat. Nos. 3,066,071 (Akers et.al.), issued Nov. 27, 1962, 3,222,252 (Kraus), issued Dec. 7, 1965 (but see Philpot et.al., *J. Dairy Science* 58:205–216), 3,993,777 (Coughman et.al.), issued Nov. 23, 1976, 4,049,830 (Pugliese), issued Sept. 20, 1977, 4,199,564 (Silver et.al.), issued Apr. 22, 1980, 4,311,709 (Dybas et.al.), issued Jan. 19, 1982, and 4,113,854 (Andrews et.al.), issued Sept. 12, 1978. A teat "sealer" similar or identical to the Andrews et.al. film-forming composition is in commercial use and has been discussed in the dairy science literature. See, for example, Farnsworth et.al., J. Am. Vet. Med. Asso. 177:441 (1980) and Farnsworth et.al., The Bovine Practitioner No. 16, pp. 28–29 (1981). Still further examples of barrier-type film-formers for bovine teats can be found in Canadian Patent 1,065,254 (Cromac Chemical Co. Ltd.), issued Oct. 30, 1979 and European published application 0 025 640 (DEVRO INC.), published Mar. 25, 1981.

Intramammary treatment of cow teats has also been proposed. See U.S. Pat. Nos. 3,912,806 (Dowrick et.al.), issued Oct. 14, 1975, 3,917,818 (Botes), issued Nov. 4, 1975, and 4,401,666 (Wedig et.al.), issued Aug. 30, 1983.

SUMMARY OF THE INVENTION

It has now been found that a particular grade or mixture of grades of partially hydrolyzed polyvinyl alcohol is a surprisingly effective, long-lasting film-former for a teat coating or sealing composition and yet is easily removable with a warm water rinse, is compatible with a variety of antimicrobial agents and coloring agents and opacifiers, and is durable enough (despite its water sensitivity) to be resistant to premature loss under a variety of actual field conditions, including the complete immersion in water which occurs when a cow goes swimming.

A key aspect of this invention involves the selection of a partially hydrolyzed grade of polyvinyl alcohol i.e. a polyvinyl alcohol containing at least about 2 mole-% residual vinyl acetate units. Film-forming coating compositions of this invention are aqueous and can be applied in essentially the same manner as other water based teat sealers. The coating compositions of this invention therefore comprise:

A major amount of an aqueous solvent medium;

More than 1% but less than about 16% by weight of a 10 partially hydrolyzed grade of polyvinyl alcohol dissolved in the water; and An antimicrobially effective amount of an aqueous polyvinyl alcohol-compatible antimicrobial agent.

It is preferred to include an opacifying amount (preferably not more than about 10 wt.-%) of an opacifying agent, and it is particularly preferred to include a coloring agent (such as a food grade dye) in this aqueous composition. Minor amounts of conventional teat dip ingredients can also be included.

After the teats have been coated with the composition of this invention, the resulting coating is permitted to dry to an adherent solid film on the teats. Typically, some of the still-liquid coating material flows down to the teat end where a plug-like deposit is formed. This deposit or plug also dries to form an adherent solid. It is believed that this plug alone is capable of sealing off the teat canal; moreover, the plug dissolves more slowly in water than the film extending upward from it, and it is easy to check and see if the teat is still protected by looking at the teat end to see if the plug is still there.

The film and the plug are, however, removable without tedious physical steps such as peeling. A warm-water wash is fully effective for the removal of the coating. (When the coating contains colorant, complete removal is observed rather easily, particularly if the colorant is blue or some other color which sharply contrast with the color of the animal's skin.)It normally requires only a few minutes of rinsing with water heated to moderate (non-scalding) temperatures.

DETAILED DESCRIPTION

Since dairy farmers are fully accustomed to the use of teat dips, dipping the teats in a cup or other receptacle containing a composition of this invention is the preferred method of applying a coating to the animal's skin. The practice of post milking teat disinfection has long been used as an effective method for preventing intra mammary infections with many bacterial pathogens, but recently researchers have shown particularly great interest in teat sealers, which are intended to provide protection between milkings and are intended for continuous wide-spread use in a herd. This prophylactic type of treatment for mastitis is the major focus of this invention. The film which forms on the surface of the teat skin serves as a shield or barrier through which mastitis-causing organisms cannot penetrate. The high degree of adherence of the film to the teat skin, even under adverse environmental conditions, is considered to be very surprising, particularly since the film has sufficient water sensitivity to be removed completely and rather quickly with a warm-water rinse or wash. This extremely convenient form of removal is particularly well adapted to practices followed by many dairy farmers, who wash the udders of their cows with a warm-water rinse on frequent occasions, e.g. before milking.

The person skilled in the art can easily test the sensitivity to warm water of films formed from compositions of this invention by simulating the coating method described above. For example, instead of actually coating the teats of an animal, one can cast a film onto a convenient inanimate substrate. Film thicknesses can range up to 300 or 400 micrometers (e.g. 12 mils), if desired. The polyvinyl alcohol literature describes the solubilization of cast films of about 10 micrometers in thickness with water temperatures ranging from room temperature up to the boiling point. Accordingly, the 10 micrometer thick cast film standard has been selected for convenience.

According to this standard, a partially hydrolyzed grade of polyvinyl alcohol useful in the claimed invention has the following characteristics.

In water heated to 75° C., 60° C. and 40° C., the 10 micrometer-thick cast film dissolves completely in less than 20 seconds, 60 seconds, or four minutes, respectively. For the sake of the comfort of the animal, water temperatures below 60° C. (preferably <40° C.) are used in the warm-water rinse. Even at temperatures below 40° C., preferred partially hydrolyzed grades of polyvinyl alcohol employed in this invention can (in 10 micrometer thick films) dissolve in less than a minute, more typically less than 10 or 20 seconds.

As is known in the art of polymer chemistry, water is the best solvent for polyvinyl alcohol. However, a "fully hydrolyzed" or "super-hydrolyzed" grade of polyvinyl alcohol tends to be far less water sensitive than the less completely hydrolyzed grades. For example, a polyvinyl alcohol which contains less than 2 mole-% residual vinyl acetate units, when cast into a thick film may have essentially complete resistance to redissolving in water, unless the water is at or near 100° C. A commonly held theory in the art is that the free OH groups of the fully hydrolyzed polymer form weak crosslinks (e.g. through hydrogen bonding) and thereby acquire some of the characteristics of cross-linked polymers. When more than 2% residual vinyl acetate units are present, however, even this weak cross-linking appears to be blocked by the acetate groups at least to a significant degree. This invention is not bound by any theory, however.

It is not fully understood why compositions of this invention, despite their water sensitivity, are capable of resisting premature loss of adherence under wet environmental conditions. (On very rare occasions, some loss of coating may be observed when a cow goes swimming in relatively warm water, e.g. in a small pond on a summer day.) Although this invention is not bound by any theory it is presently believed that the concentration of partially hydrolyzed polyvinyl alcohol in the coating composition of this invention is somehow related to this resistance to premature redissolving in wet environments. The aforementioned polyvinyl alcohol concentration has been selected to provide coatings of sufficient thickness to last between milkings without resulting in a composition viscosity which is too high to permit sufficient wetting out on teat skin.

These and other aspects of the coating composition of this invention will now be discussed in greater detail.

The Composition

A preferred bovine teat coating composition of this invention contains at least about 2 or 3 but less than about 12% by weight of partially hydrolyzed grade polyvinyl alcohol. To provide opacity to the composition, a suitable aqueous latex is included in the composition. There are thus at least two ways to determine how much opacifier can be added; first, one can select a polymer latex of suitable solids content and add a certain percentage of that latex; alternatively, one can look to the amount of emulsoid or dispersoid or suspensoid organic polymer solids distributed uniformly through the aqueous coating composition after the latex has been blended in and has lost its separate identity. Using the latter approach, the composition of this invention can contain about 0.2 to 10% by weight of the opacifying solids distributed uniformly through the aqueous solvent medium in which the partially hydrolyzed polyvinyl alcohol is dissolved.

The preferred amount of antimicrobial agent dissolved in this aqueous solvent medium is about 0.1 to 10% by weight of the coating composition. It is preferred that the antimicrobial agent be water soluble in these concentrations.

Accordingly, >65%, e.g. at least about 80% by weight of the coating composition will normally be water. Up to about 96 or 97% by weight of the composition can be water if the fewest possible ingredients are used in amounts just adequate for the objectives of this invention. Manageable coating composition viscosities can be obtained throughout this range.

The theoretical monomer, vinyl alcohol, does not exist and hence cannot be polymerized; polyvinyl alcohol, sometimes referred to as poly(vinyl alcohol), is made from polyvinyl acetate by hydrolysis. The physical properties of polyvinyl alcohol are controlled by the molecular weight and the degree of hydrolysis. As a practical matter, the most common available grades of polyvinyl alcohol, ranked by degree of hydrolysis, are an 87-89% grade (containing 11-13 mole percent residual vinylacetate units), a 96% hydrolysis grade (containing 4 mole percent residual vinyl acetate units), and the "fully hydrolyzed" and "superhydrolyzed" grades, which are about 98% and greater-than-99% hydrolyzed, respectively. Lower degrees of hydrolysis (e.g. 74% and 79%) are also commercially available. Moreover laboratory data are available on grades as low over 74-80% in degree of hydrolysis (20-26 mole percent as residual vinylacetate units). Because of the variety of grades either known in the literature or commercially available, one skilled in the art can formulate a polyvinyl alcohol solution having an average degree of hydrolysis ranging from 74 to more than 99% simply by blending the known or commercial grades in any desired ratios. Accordingly, the term "partially hydrolyzed grade polyvinyl alcohol", as used in this description should be understood to include both a single grade and a mixture of grades, and the term "average degree of hydrolysis" should be understood to refer to the degree of hydrolysis arrived at by averaging (with appropriate weighting on the basis of proportions) the partially hydrolyzed grades in the mixture, if a mixture is used, or the average degree of hydrolysis of a single grade, if a single grade is used (an "88% grade", for example, may be the average of a spectrum ranging from 87 to 89% within the same grade).

All commercial polyvinyl alcohol grades have some solubility in water, but as noted previously, fully hydrolyzed products must be heated close to the atmospheric boiling point of water to achieve complete solution. After the polymer in such solutions has formed a thick film, redissolving in water may be very difficult unless boiling water is used. A partially hydrolyzed polyvinyl alcohol containing 20-25% residual vinylacetate units, on the other hand, dissolves fully in cold water. (There is a risk that the dissolved polymer may precipitate if the solution is heated, however.) The hydrolysis range of 87-89% is generally considered optimum for both cold- and hot-water solubility by those in the art.

The particle size of the solid polyvinyl alcohol powder—as well as molecular weight and crystallinity—have an effect upon solubility. In the context of this invention, however, the most important factor is the degree of hydrolysis. The preferred average degree of hydrolysis ranges from 70 to 96 mole-percent, the optimum occurring somewhere between 85 and 90 mole-percent, e.g. 87-89%. These partially hydrolyzed grades or mixtures of grades exhibit good compatibility with a variety of antimicrobial agents, opacifying agents, emulsifiers and surfactants, water soluble salts or electrolytes, and the like.

The concentration of the partially hydrolyzed grade vinyl alcohol polymer in a film-forming coating composition of this invention is of great importance. The lower-level of concentration (near 2% by weight) is generally governed by the desired thickness on the teat skin. A polyvinyl alcohol concentration much less than 2% by weight typically results in a teat coating which is too thin to last between milkings. The upper limit of polymer concentration tends to be governed by viscosity. A partially hydrolyzed grade polyvinyl alcohol centration greater than 16% has a viscosity which is typically too high to permit sufficient wetting out on the teat skin. A particularly useful range of concentration is 2–8% by weight of partially hydrolyzed grade polyvinyl alcohol, and the optimum concentration appears to be at or near 5% by weight. A concentration of 2 or 3% by weight is adequate for some purposes but may be subject to premature solubilization when the animal goes swimming, particularly if the body of water is warm. The risk of premature solubilization at concentrations of 5% or higher appears to be very low and entirely within limits acceptable to dairymen. As noted previously, loss of teat sealer coatings between milkings are easily detected and quickly remedied if the coatings contain a high-visibility coloring agent.

The concentration of coloring agent is not critical. Concentrations as low as 10 ppm by weight impart visible color although concentrations 0.001% by weight or higher are preferred. The preferred color is blue, and there are blue dyes of negligible toxicity or even of edible quality which are commercially available. A dried film which is blue in color cannot be easily mistaken for mastitic milk. Similar considerations apply to dyes which are red or green or the like.

A dried film comprising a coating composition of this invention may nevertheless be difficult to see on the teat skin if no opacifying agent is included in the composition to overcome its virtually total transparency. Polyvinyl alcohol in the partially hydrolyzed grades used in this invention forms true solutions in water which are both colorless and transparent; hence, the opacifying agent greatly assists the coloring effect provided by the dye or other coloring agents. There are several factors which influence the selection of the type and amount of opacifier included in the coating compositions of this invention. The preferred opacifying agents are in the form of aqueous latexes before being introduced into a composition of this invention. An "aqueous latex", in this context comprises suspensoid or, more preferably, dispersoid or emulsoid particles of a suitable synthetic organic polymer. Suspensoid particles are not preferred due to their tendency to settle out of the aqueous suspending medium. Dispersoid particles are typically too small in size to settle out, and emulsoid particles resist settling out due to surface active phenomena. Emulsoids can be either self-emulsified (e.g. by ionically-charged or other hydrophilic sites on the polymer molecule) or kept in an emulsified state by a separate surface active agent. The solids content of a suitable latex can range from 15–70% by weight, most typically 30–60% by weight. The polymer solids can be either homopolymers or copolymers and can, if desired, include polyelectrolyte blocks or randomly-distributed units of a polyelectrolyte. The latex should be selected for compatibility (e.g. stability or resistance to precipitation or settling) with partially hydrolyzed polyvinyl alcohol, particularly the partially hydrolyzed grades containing at least 4% residual vinylacetate units. The effect of the antimicrobial agent upon latex stability should also be taken into account.

In addition to stability, degree of opacity, and compatibility with the other ingredients of the coating composition, the effect of the opacifier upon the flexibility of the dried film should be carefully considered. The most effective protection of the teat is provided with a relatively flexible film. At high concentrations, some opacifying agents may detract from this flexibility. This problem may be particularly acute with inorganic fillers and opacifiers such as finely divided silicates (clay or the like). For this reason, it is generally preferred to exclude inorganic fillers and opacifiers from compositions of this invention.

The preferred latexes contain fine dispersions or emulsions of styrene copolymers, e.g. styrene/acrylate, styrene/acrylamide, or styrene/polyvinyl pyrrolidone. The last of these three is considered the most compatible with partially hydrolyzed grades of polyvinyl alcohol and the preferred antimicrobial compounds. In the case of, for example, a 40% percent solids latex, the optimum concentration of latex is generally within the range of 0.5–3%, 2% being at or near the optimum concentration. At concentrations below 0.5%, the dried film may still be difficult to see. At concentrations greater than 3%, the latex may detract somewhat from the flexibility of the dried film.

Somewhat similar considerations apply to the selection of the amount and type of antimicrobial agent, but in addition, the antimicrobial agent should be effective against certain gram-positive and gram-negative bacteria in the desired concentration range. The dairy science literature contains extensive reviews and original work relating to the species of microorganisms which have mastitis causing properties These species include (but are not limited to) various coliform organisms (such as *Escherichia coli*), gram-positive bacteria such as *Staphylococcus sp.* and *Streptococcus sp.* or gram-negative bacteria such as *Pseudomonas sp.* The most common mastitis-producing organisms (besides the coliforms) include *Ps. aeruginosa*, *Staph aureus*, and *Strep. agalactiae*. According to the National Institute of Research in Dairying in Reading, England, over 90% of mastitis infections are caused by *Staph. aureus* and various species of *Strep.*, including *Strep. agalactiae* (and to some extent, *Strep. dysgalactiae* and *Strep. uberis*). Various antimicrobial agents have been suggested for bovine mastitis in the, scientific and patent literature, including iodophors hypochlorites and other chlorine-releasing agents, bromine, hydroxy-quinone, ammonium chloride, chlorhexidine and chlorhexidine salts, hexachlorophene, diaphene, cetyl pyridinium chloride, and various other quaternary ammonium germicidal salts It has also been discovered that certain surface active agents have sufficient antimicrobial properties to be used in teat disinfectant compositions.

The bactericide chlorhexidine is also known as bis(p-chlorophenyl-diguanido)hexane, which is also available as diguanide (biguanide) or guanyl guanidine salts. These salts are water soluble in convenient concentrations, e.g. 5–25% by weight. The gluconate salt of chlorhexidine is an extremely safe and effective broad-spectrum antimicrobial agent known to be useful in topical preparations—and known to be effective against gram-positive and gram-negative bacteria and other pathogens. The action of chlorhexidine gluconate is typically characterized by rapid bactericidal and sustained bacteriostatic effects and has been proven to be well suited to teat dips used to reduce the incidence of bovine mastitis. This catatonic bactericide, in its gluconate salt form is nearly neutral when dissolved in water; that is, the water solutions have a pH near 7.0. These salts have been found to be fully compatible with the partially hydrolyzed grades of polyvinyl alcohol and the opacifiers used in this invention. Concentrations of this antimicrobial agent can range from 0.1 to 10% by weight, but are preferably within the range of 0.2–6% by weight. When introduced into the teat sealer compositions of this invention as a water solution (e.g. a 20 percent wt./v. aqueous solution), the ideal amount of this solution appears to be 2% by weight of the total composition. This concentration provides a high level of bactericidal and bacteriostatic activity without unduly increasing the cost of the composition. (The increase in activity obtained by using higher concentrations does not presently appear to be cost-justified.)

This preferred antimicrobial agent is commercially available in solution form.

Other highly useful antimicrobial compounds are derivatives of alkylene diamines and can be, for example, (higher alkyl)alkyleneamino glycines or the like. (Typical higher alkyl groups contain 7-24 carbon atoms.) Typical compound of this type have the structural formula:

R—NH-A-NH$_a$ CH$_2$COOH wherein R is a higher alkyl group (such as dodecyl), A is a lower alkylene bridge (ethylene, propylene, etc.), and a is a small number within the range of 1-6, e.g. 1 or 2. Examples of these compounds are dodecyl diethylene -diamino glycine and dodecyl aminopropyl glycine.

When the above-described components are combined into a suitable aqueous composition, the viscosity of the composition can range from as low as about 25 or 30 centipoise (cps) to as high as 1,000 or 2,000 cps. No phase separation effects have been observed when the antimicrobial compound is a chlorhexidine salt, an alkylene diamine derivative of the type described above, or one of the zinc salts known to be useful in teat dip compositions.

Other conventional teat dip or teat sealer ingredients can, if desired, be included in compositions of this invention, emollients, viscosity control agents and/or thickeners (such as cellulosic gums and the like), surface-active agents, antifoaming agents, etc. It is, however, ordinarily preferred not to provide too great a thickening effect which might detract from the ability of the composition to wet out teat skin. Viscosities in the range of 20-1000 cps (e.g. 50-500 cps) are preferred for this reason.

The compositions described above are resistant to premature solubilization under a variety of environmental conditions, but are readily removed by a warm-water rinse, e.g., the type of rinse used by dairy farmers prior to milking. These compositions generally have good freeze-thaw stability and retain their antimicrobial activity after heat aging.

If the compositions of this invention contain a thickener (e.g. an amount from 0.05 to 5 wt.-%), nonionic hydrophilic polymers such as cellulose ethers (e.g. hydroxyethyl cellulose) are preferred. The known emollients include polyhydric alcohols, both liquid and solid (glycerin, sorbitol, etc.), polyvinyl pyrrolidone, lanolin fractions or derivatives, and other materials disclosed in U.S. Pat. No. 3,993,777 cited previously (e.g. esters, glycol derivatives, vegetable and mineral oils, and long-chain monohydric alcohols). A percent or so of emollient can be effective, and amounts in excess of 5 wt.-% are generally unnecessary.

Typically a thickener is not needed, because adequate viscosity can be obtained simply by adjusting the amount of polyvinyl alcohol in the teat sealer composition. Concentrations of polyvinyl alcohol less than 8 wt.-% tend to be very thin and run down the sides of the teat very quickly without leaving a heavy film. Surprisingly, however, the plug-like deposit which forms at the bottom of the teat is so strongly adherent that the potentially heavier films provided by 8-16% polyvinyl alcohol compositions are not needed; moreover, the superior wetting action of 4-6 wt.-% concentrations is desirable The following non-limiting Examples illustrate the principle and practice of this invention.

EXAMPLE 1

The following composition was prepared and found to be stable and resistant to phase separation.

| | |
|---|---|
| "VINOL 540" (trademark for 87-89% hydrolysis grade of polyvinyl alcohol; Brookfield viscosity in 4% aq. soln., using Model LVF No. 1 spindle, 60 rpm, 20° C. = 35-45 cps, pH = 5 to 7 5% max. volatiles, ash = 0.3% max., APHA Col. = 30 max.) | 5.000 wt. % |
| Chlorhexidine gluconate (aq. 20 wt/vol %) | 2.000 wt. % |
| "WITCOPAQUE R 11" (styrene/acrylate copolymer aqueous latex, 40% solids, pH = 6.7-7.3 density = 1.04 g/ml) | 2.000 wt. % |
| FD & C #1 dye (Brilliant Blue FCF, powdered solid) | 0.005 wt. % |
| Water, deionized | 90.995 wt. % |
| | 100.000 wt. % |

FD & C # 1 dye is the disodium salt of 4-{[4-ethyl-p-sulfobenzyl-amino) -phenyl] - (2-sulfonium-phenyl) - methylene} - [1 - (N - ethyl - N -p - cyclohexa - 2,5 - dienimine]. It is a food grade blue dye having the Color Index (1956) number 42090 and is available as a powder comprising 84-94% pure dye.

The above-described composition had the following properties:

| | |
|---|---|
| Brookfield Viscosity (2/20/20° C.): | 99 ± 10 cps |
| Density (at 20° C.): | 1.0133 g/ml |
| pH: | 5.60 |

The composition was prepared by charging the water to the mixing vessel first, following by adding the partially hydrolyzed (87-89%) grade of polyvinyl alcohol, while stirring. The water was then heated to 77° C. for 30 minutes. The remaining three ingredients were then added, with stirring, along with enough water to bring the water content to 90.995% by weight.

| | |
|---|---|
| "VINOL 540" (87-89% hydrolyzed grade of polyvinyl alcohol, see Example 1) | 8.00 wt. % |
| Chlorhexidine gluconate (aq. 20 wt/vol %) | 2.00 wt. % |
| Opacifier: POLECTRON ® 430, trademark for non-toxic (LD$_{50}$ > 40 g/kg) non-irritating styrene-polyvinyl pyrrolidone latex of 38-41% solids, emulsoid particle size: 90% < 0.5 μM; Brookfield viscosity: ≦750 cps at 25° C. (spindle No. 3, 30 rpm); pH = 2.0-5.0; spec. grav. (25° C.): 1.04 | 2.00 wt. % |
| FD & C #1 dye (blue food-grade dye) | 0.01 wt. % |
| Water, deionized | 87.99 wt. % |
| | 100.00 wt. % |
| Brookfield viscosity (3/20/20° C.): | 910-950 cps |

The above-described formulation exhibited greater adherence to cow teats when the tests were immersed in water, as compared to the formulation of Example 1, but the Example 2 formulation was nevertheless removable with a warm water rinse.

EXAMPLE 3

The procedure of Examples 1 and 2 was utilized to prepare the following composition:

| | |
|---|---|
| "VINOL 540" (87–89% hydrolyed polyvinylalc.; see Example 1) | 5.00% |
| Chlorhexidine gluconate (aq. 20 wt./vol. %) | 2.00% |
| Opacifier (POLECTRON ® 430, trademark for styrene-polyvinyl pyrrolidone latex; see Example 2) | 2.00% |
| FD & C #1 dye | 0.01% |
| Water, deionized | 90.99% |
| | 100.00% |

This composition was found to be very similar to that of Example 1; it was stable, resistant to phase separation and a good performer in the field.

EXAMPLE 4

Compatibility Testing

The purpose of this Example was to test the compatibility of polyvinyl alcohol solutions (at 10 wt.% solids in water) with the following biocides in the indicated biocide concentrations.

TABLE I
BIOCIDES

| Biocidal Agent | Concentration (wt./wt. % in 10 wt./wt. % polyvinyl-alcohol solution |
|---|---|
| Chlorhexidine gluconate, 20% (wt/vol.) | 5.0 |
| MONOQUAT P-TL (Mona Ind. trademark for quaternary ammonium bactericide) | 1.0 |
| MONOQUAT P-TC (see "P-TL") | 1.0 |
| BTC 2125M (Onyx, quaternary ammonium salt) | 1.0 |
| Zinc Omadine (Olin, zinc pyridine thione) | 2.0 |
| "TEGO 51B" (trademark for dodecyldiethylene diaminoglycine + dodecylaminopropylglycine) | 0.5 |

The concentrations for these biocides listed in the above Table have been shown to be efficacious in killing mastitis-causing organisms.

The polyvinyl alcohol solutions used were adjusted to 10% (wt/wt) solutions starting from the commercially available materials VINOL 523 and VINOL 540, both of which are 87–89% hydrolyzed, the VINOL 523 having the same properties as VINOL 540 (see Example 1), except for a somewhat lower Brookfield viscosity, i.e. 21–25 cps (measured in 4% aq. sol'n, Model LVF Viscometer, #1 spindle/160 rpm/20° C.).

The 10 wt/wt% polyvinyl alcohol solutions were found to be compatible with all of the biocidal agents listed in Table I, above.

EXAMPLE 5

Sanitizing Efficiency

The teat dip biocidal activity test method proposed by the National Mastitis Council, Guideline E (Nov. 1, 1977) was used, except for the organic load part of the test. One milliliter (ml) of bacterial culture was added to separate 99 ml aliquots of the composition of Example 1. At time limits of 30 seconds and 2 minutes, 1 ml amounts are removed and mixed in 9 ml of neutralizer. Aliquots of the neutralizer mixture were plated in Fluid Thioglycollate Medium (Difco Laboratories, Detroit, Mich., U.S.A.) and incubated at 37° C. for 72 hours. Resultant colonies were counted. Each test was done twice ("Test #1" and "Test #2").

The challenge microorganisms were:
(1) *Escherichia coli* #11229,
(2) *Pseudomonas aerugionosa* #15442
(3) *Staphylococcus aureus* #6538
(4) *Streptococcus agalactiae* #13813

TABLE 2

| | | Biocidal Activity | | | |
|---|---|---|---|---|---|
| | Numbers | Test #1 | | Test #2 | |
| Organism | Control | 30 Sec. | 2 Min. | 30 Sec. | 2 Min. |
| (1) (E. coli) | 10 × 10$^7$ | Survivor Count: 2 =99.999% kill | Survivor Count: <1 =99.999% kill | Survivor Count: 2 =99.999% kill | Survivor Count: 3 =99.999% kill |
| (2) (Ps. Aerug.) | 16 × 10$^7$ | Survivor Count: <1 =99.999% kill | Survivor Count: <1 =99.999% kill | Survivor Count: <1 =99.9999% kill | Survivor Count: 2 =99.999% kill |
| (3) (Staph. aureus) | 9.9 × 10$^7$ | Survivor Count: 453 =99.999% kill | Survivor Count: 16 =99.999% kill | Survivor Count: 1256 =99.999% kill | Survivor Count: 18 =99.999% kill |
| (4) (Strep. agalact.) | 8 × 10$^7$ | Survivor Count: 4 =99.999% kill | Survivor Count: 0 =100% kill | Survivor Count: 3 =99.999% kill | Survivor Count: 2 =99.999% kill |

The above described tests were repeated with the compositions of Examples 2 and 3 (vs. organisms [1]–[3]); similar results were obtained, except the % kill in the case of Example 3 was even better (consistently 100%) vs. Escherichia coli and Ps. aeruginosa.

EXAMPLE 6

Freeze-Thaw Stability

The compositions of Examples 1, 2, and 3 were tested for freeze-thaw stability. All three compositions were found to be stable.

EXAMPLES 7a and 7b

The purpose of these Examples was to:
a. determine the effects of using small concentration of partially hydrolyzed polyvinyl alcohol in compositions similar to the compositions of Examples 1–3, except that the antimicrobial agent was 1.5 wt.-% "TEGO 51 B" (see Example 4), the opacifier was omitted, and 0.1 wt.-% "FOAMAS- TER VF" (an anti-foaming agent) was included; the amount of dye was 0.10 wt.-%.

b. determine the effects of using partially hydrolyzed polyvinyl alcohol having as much as 26% residual vinyl acetate units (74% grade, trade designation "MOWIOL 10–74") and 21% residual vinyl acetate units (79% grade, trade designation "MOWIOL 15–79"), and as little as about 2% vinyl acetate units ("fully hydrolyzed" or "98%" grade "VINOL 107") and less than 1% vinyl acetate units ("super-hydrolyzed" or 99.3% grade, "VINOL 165")

EXAMPLE 7a

It was found that formulations containing only 2 wt. and 3 wt.-% polyvinyl alcohol ("VINOL 540") did form films on glass tubes and excised cow teats (obtained from a slaughter house). At the ends of the tubes and the excised teats, these low-percentage formulations also formed plug-like deposits. When compared to similarly obtained films and plugs of a 5 wt.-% polyvinyl alcohol ("VINOL 540") formulation, it was found that the films of the 5% formulation took 60% longer to dissolve than the 2 and 3% formulations. In the context of the invention, the 60% longer dissolving time was considered a beneficial safeguard against premature loss of the film. However, the plugs of the 2% and 3% formulations resisted dissolution fairly well better and were considered to be marginally sufficient for use in this invention.

EXAMPLE 7b

The 74% and 79% grades of polyvinyl alcohol were found to perform in a manner very similar to the preferred 88% grade ("VINOL 540"), at a concentration of 5% by weight of the total composition. However, the "fully hydrolyzed" ("VINOL 107") grade was almost excessively slow in dissolving, and hence, at best, only marginally useful in this invention. Films of the formulation containing 5% VINOL 107 took 2.5 times longer to dissolve and the plug took 5 times as long to dissolve.

The "super-hydrolyzed" grade ("VINOL 165") could not be used in this invention, because, absent scraping or agitation, the plug on the end of the tube or teat would not dissolve even after 3 hours of observation.

What is claimed is:

1. A method for the prophylactic treatment of mastitis in a dairy cow in between milkings, said method comprising the steps of:

A. coating the teats of the cow with an aqueous composition comprising:
  at least about 2% but less than about 12% by weight of partially hydrolyzed grade polyvinyl alcohol having an average degree of hydrolysis ranging from about 70 to 96 mole-%;
  from 0% to about 10% opf an opacifier comprising emulsoid, dispersoid, or suspensoid polymer solids distributed uniformly through the water of said aqueous composition;
  about 0.1% to 10% by weight of an antimicrobial agent, said antimicrobial agent being a biguanide salt, an (alkyl)alkylenaminoglycine, a quaternary ammonium salt, zinc pyridine thione, or combinations thereof; and
  at least 65% water;

B. permitting the resulting coating to flow down to the teat end and form a plug-like deposit which is more resistant to solution in water than the film extending upward from it and to dry to form an adherent film on the teats, whereby the resulting adherent film and said plug-like deposit are removable with water, the adherent film being more easily removable than said plug-like deposit;

C. prior to milking the dairy cow, removing said adherent film and said plug-like deposit by means of a water wash with water heated to non-scalding temperatures moderately elevated above room temperature.

2. A method according to claim 1, herein said aqueous composition contains up to about 0.5% weight of a coloring agent.

3. A method according to claim 1, wherein the aqueous composition comprises:
  dissolved in the water of said composition, 2–8% by weight of partially hydrolyzed grade polyvinyl alcohol having an average degree of hydrolysis of at least about 74 but less than about 90 mole-%,
  dissolved in said water, 0.2–6% by weight of a said antimicrobial agent,
  uniformly distributed through said water, 0.14 3% by weight of an opacifying latex containing 15–70% by weight organic polymeric latex solids, said latex solids being comparable with 2–8 weight-% partially hydrolyzed grade polyvinyl alcohol solutions,
  dissolved in said water, up to 0.5% by weight of a substantially water-soluble dye which provides a color contrasting sharply with white; and
  dissolved in said water, 0–5% by weight of an emollient;
  substantially the balance of said composition being water.

4. A method according to claim 3, wherein said aqueous composition contains at least about 0.5% by weight of said opacifying aqueous latex.

5. A method according to claim 3, wherein said antimicrobial agent is a biguanide salt or an (alkyl)alkylenaminoglycine.

6. A method according to claim 5, wherein said antimicrobial agent chlorhexidine gluconate.

7. A method according to claim 3, wherein said aqueous composition contains at least 0.0001% by weight of the substantially water-soluble dye.

8. A method according to claim 1, wherein a 10 micrometer-thick cast film of said partially hydrolyzed grade of polyvinyl alcohol has the following characteristics:
  in water heated to 75° C., the cast film dissolves completely in less the 20 seconds; in water heated to 60° C., the cast film dissolves completely in less than 60 seconds; and in water heated to 40° C., the cast film dissolves completely in less than 4 minutes.

9. A method according to claim 1, wherein said aqueous composition has a viscosity of at least about 25 centipoise, but no more than about 2,000 centipoise, at 20° C.

10. A method according to claim 9, wherein said viscosity is no more than 1000 cps at 20° c.

11. A method according to claim 1, wherein the aqueous composition used to coat the teats of the cow in said step A is stable and resistant to phase separation after freezing and thawing.

* * * * *